United States Patent [19]

Walker

[11] Patent Number: 4,670,621

[45] Date of Patent: Jun. 2, 1987

[54] CATALYTIC SYNTHESIS OF OLEFINS FROM PARAFFINS

[75] Inventor: Howard W. Walker, Baton Rouge, La.

[73] Assignee: Ethyl Corporation, Richmond, Va.

[21] Appl. No.: 859,696

[22] Filed: May 5, 1986

[51] Int. Cl.$^4$ .............................................. C07C 5/02
[52] U.S. Cl. ................................. 585/656; 585/257; 585/277; 585/616; 585/661
[58] Field of Search .............. 585/656, 616, 660, 661, 585/654, 257, 277

[56] References Cited

U.S. PATENT DOCUMENTS

| | | | |
|---|---|---|---|
| 3,524,898 | 8/1970 | Beirne | 585/656 |
| 3,721,718 | 3/1973 | Hughe et al. | 585/645 |
| 3,849,510 | 11/1974 | Maspero et al. | 585/616 |
| 4,191,846 | 3/1980 | Farha, Jr. et al. | 585/660 |
| 4,361,497 | 11/1982 | Boldt et al. | 585/645 |

OTHER PUBLICATIONS

Crabtree et al., J. Am. Chem. Soc., 104, pp. 107–113 (1982).
Crabtree et al., J. Am. Chem. Soc., 104, pp. 6994–7001 (1982).
Crabtree et al., J. Am. Chem. Soc., 101, pp. 7738–7740.
Moseley et al., J. Chem. Soc., Part A, pp. 2875–2883 (1970).

Primary Examiner—Asok Pal
Attorney, Agent, or Firm—Donald L. Johnson; John F. Sieberth

[57] ABSTRACT

Saturated hydrocarbon is transformed catalytically into olefinic hydrocarbon of corresponding skeletal configuration by reacting the saturated hydrocarbon with a suitable alkene cyclopentadienyl or alkene arene transition metal molecular complex, such as bis(ethylene)pentamethylcyclopentadienyliridium, in the presence of free alkene as hydrogen acceptor. The reaction may be performed photochemically under irradiation with ultraviolet light or it may be performed thermolytically under application of heat. The catalyst may be charged to the reaction as a preformed alkene cyclopentadienyl or alkene arene transition metal molecular complex or the catalyst may be formed in situ in the reaction mixture via displacement of ligand from a suitable transition metal complex containing the displaceable ligand, such as dicarbonylpentamethylcyclopentadienyliridium or cyclooctadienepentamethylcyclopentadienyliridium.

12 Claims, No Drawings

CATALYTIC SYNTHESIS OF OLEFINS FROM PARAFFINS

In one of its forms this invention relates to activating carbon-hydrogen bonds of a saturated hydrocarbon with an ethylene molecular complex of a transition metal in the presence of gaseous ethylene so that olefinic hydrocarbon corresponding in skeletal configuration to the saturated hydrocarbon is formed. Ethane is coproduced in the process, and thus ethylene is caused to serve as a hydrogen acceptor. This was a singularly unexpected discovery. Ethylene has been regarded heretofore as an ineffective hydrogen acceptor in attempts to dehydrogenate alkanes with transition metal complexes. See R. H. Crabtree, "The Organometallic Chemistry of Alkanes", *Chem. Rev.*, 1985, 85, 245–269, page 253. Indeed, t-butylethylene was previously considered to be one of the very few olefins that is an effective hydrogen acceptor in reactions of this type, and according to Crabtree (loc. cit.) its usefulness "was only discovered after an extensive search".

Pursuant to another embodiment of this invention, saturated hydrocarbon (i.e., paraffin or cycloparaffin or both) is transformed catalytically to olefinic hydrocarbon by transferring hydrogen from the saturated hydrocarbon to a free alkene via a bis(alkene)cyclopentadienyl transition metal molecular complex or a bis(alkene)arene transition metal molecular complex so that olefinic hydrocarbon corresponding is skeletal configuration to the saturated hydrocarbon is formed. In essence, the paraffinic or cycloparaffinic carbon-hydrogen bonds are transformed into the activated carbon-hydrogen bonds of the catalyst and thence are transferred to the free olefin serving as the hydrogen acceptor. Because of the catalyst employed, it is now deemed possible to use alkenes in general as hydrogen acceptors—a feat which has not been possible heretofore. In short, while ethylene is the preferred alkene, other straight and branched chain alkenes, such as propylene, the butenes, the pentenes, the hexenes, the heptenes, the octenes, the decenes, the dodecenes, and the like, are deemed suitable as hydrogen acceptors in the process. The alkene preferably corresponds in skeletal structure to the alkene of the molecular complex initially present in the reaction system.

Various transition metal molecular complexes are deemed suitable for use as catalysts in the process. These include bis(alkene)cyclopentadienyl iridium complexes, diene cyclopentadienyl iridium complexes, bis(alkene)arene osmium complexes, diene arene osmium complexes, tris(alkene)cyclopentadienyl rhenium complexes, triene cyclopentadienyl rhenium complexes, and similar materials, in which the cyclopentadienyl or arene groups may be unsubstituted or substituted with appropriate groups that do not prevent the desired transformation reaction from occurring, such as alkyl, fluoro, fluoroalkyl (trifluoromethyl, etc.), and the like. A particularly preferred class of complexes are the bis(alkene)pentamethylcyclopentadienyl iridium complexes, most especially bis(ethylene)pentamethylcyclopentadienyl iridium. These catalysts are stable in air and have good thermal stability characteristics rendering them especially suitable for commercial utilization.

Bis(ethylene)pentamethylcyclopentadienyl iridium reacts with paraffins photochemically at temperatures above and below 25° C., and thermally at 160° C. and above. Thus the process may be conducted by irradiating the reaction mixture with a source of ultraviolet light (sunlamp, sunlight, pure UV light, etc.) at any convenient temperature such as room temperature or sunlight-induced temperatures. Alternatively, the process may be conducted thermally by heating the reaction mixture to a temperature at which the transformation of paraffin to olefin occurs at a suitable reaction rate. In the case of thermal reactions using bis(ethylene)pentamethylcyclopentadienyl iridium complex as the catalyst and ethylene as the hydrogen acceptor, reaction is evident at about 170° C., and proceeds at a reasonable reaction rate at about 200° C. and above in a closed system under ethylene pressure. Generally speaking, the process may be performed at any suitable pressure—subatmospheric, atmospheric, superatmospheric—so long as there is intimate contact among the components of the reaction mixture and the stability of the catalyst is not adversely affected. Thus with gaseous alkenes its is desirable to perform the reaction at a superatmospheric pressure, for example up to about 1,000 psi partial pressure or more. The temperatures used in the process may range upwards as high as 300° C. or more. Naturally one should not use a temperature and pressure that will lead to thermal decomposition of the catalyst, reactants or products of the particular reaction mixture being employed.

It is possible to prepare the transition metal complexes in situ by charging to the initial reaction system an appropriate cyclopentadienyl or arene molecular complex of the transition metal (rhenium, osmium and, preferably, iridium) having ligands that are displaced by the alkene. However when resorting to this practice, care should be exercised to select a complex which does not contain ligands that materially inhibit or suppress the desired paraffin-to-olefin transformation reaction. For example, complexes with hydrido or diene or triene ligands are suitable, as are complexes with carbonyl ligands, although the displaced carbonyl groups tend to exert a reaction-suppressing effect. Thus in any given case where it is desired to resort to use of an alkene cyclopentadienyl transition metal complex or alkene arene transition metal complex generated in situ in this manner, it is desirable to perform a few pilot experiments to insure that the released ligands do not adversely affect the desired reaction to any significant extent.

It is preferable to charge a transition metal complex such as a bis(alkene)cyclopentadienyl iridium complex or a diene cyclopentadienyl iridium complex to the reaction system in preformed condition. Most preferably the complex contains coordinated alkene corresponding to the free alkene to be used in the reaction. In this way the reaction mixture is devoid of significant amounts of extraneous components that would otherwise be released or formed during the reaction. However it is possible to use a complex in which the alkene initially differs from the free alkene to be used. In such cases the catalyst tends to equilibrate during the course of the reaction. Procedures that may be used or adapted for use in the synthesis of the transition metal catalysts such as the bis(alkene)cyclopentadienyl iridium complexes are reported for example by K. Moseley, J. W. Kang, P. M. Maitlis, *J. Chem. Soc.*, 1970, (A) 2875–2883, and by R. B. King, *Inorganic Chemistry*, Vol. 2 (1963) pp. 528–531.

A few exemplary catalysts which may be employed pursuant to this invention include
Bis(ethylene)cyclopentadienyl iridium Bis(ethylene)methylcyclopentadienyl iridium
Bis(ethylene)dimethylcyclopentadienyl iridium
Bis(ethylene)trimethylcyclopentadienyl iridium
Bis(ethylene)tetramethylcyclopentadienyl iridium
Bis(ethylene)pentamethylcyclopentadienyl iridium
Bis(ethylene)ethylcyclopentadienyl iridium
Bis(ethylene)diethylcyclopentadienyl iridium
Bis(propylene)cyclopentadienyl iridium
Bis(propylene)pentamethylcyclopentadienyl iridium
Bis(butene)pentamethylcyclopentadienyl iridium
Bis(hexene)pentamethylcyclopentadienyl iridium
Bis(ethylene)benzene osmium
Bis(ethylene)hexamethylbenzene osmium
Tris(ethylene)cyclopentadienyl rhenium Among suitable catalyst precursors that have displaceable ligands and that may be used to form the catalyst in situ are the following:
Cyclooctadienetrimethylcyclopentadienyl iridium
Cyclooctadienepentamethylcyclopentadienyl iridium
Hydridopropenylpentamethylcyclopentadienyl iridium
Hydridodecenylpentamethylcyclopentadienyl iridium
Dicarbonylcyclopentadienyl iridium
Dicarbonylmethylcyclopentadienyl iridium
Dicarbonyldimethylcyclopentadienyl iridium
Dicarbonyltrimethylcyclopentadienyl iridium
Dicarbonyltetramethylcyclopentadienyl iridium
Dicarbonylpentamethylcyclopentadienyl iridium
Dicarbonylethylcyclopentadienyl iridium
Dicarbonyldiethylcyclopentadienyl iridium
Tetrahydridopentamethylcyclopentadienyl iridium
Cyclooctadienehexamethylbenzene osmium
Carbonyldihydrido benzene osmium
Carbonyldihydrido toluene osmium
Carbonyldihydrido hexamethylbenzene osmium
Tetrahydridohexamethylbenzene osmium
Dicarbonylhydrido cyclopentadienyl osmium
Cyclooctatrienepentamethylcyclopentadienyl rhenium
Tricarbonylcyclopentadienyl rhenium
Tricarbonylmethylcyclopentadienyl rhenium
Tricarbonylpentamethylcyclopentadienyl rhenium The reaction is preferably performed in bulk (i.e., with no auxiliary reaction solvent or diluent). However it may be conducted in solution in a suitable relatively inert liquid reaction medium such as neo-pentane or the like. In many cases the paraffin or cycloparaffin reactant itself will serve as a solvent at least during the initial stages of the reaction.

Individual cyclic or acyclic paraffins or mixtures of different cyclic and/or acyclic paraffins may be used in the process. Likewise the feedstock may comprise mixtures of alkanes and alkenes, with or without other hydrocarbons (cycloparaffins, etc.), provided of course that the mixture has a sufficient alkane and/or cycloalkane content to make it economically feasible to subject it to processing in accordance with this invention. Use of cyclic and/or acyclic paraffinic hydrocarbons that are in the liquid state at the reaction temperature selected is preferred as this enables the reaction to be performed without use of an auxiliary reaction solvent or diluent. Thus paraffins and cycloparaffins of up to 100 or more carbon atoms may be used in the process. A preferred range is $C_6$ to $C_{24}$.

Proportions of the reaction components used are largely discretionary so long as there is enough alkene present to serve as acceptor for the hydrogen abstracted from the paraffinic reactant and to prevent catalyst decomposition.

The practice and advantages of this invention will be still further apparent from the following illustrative examples.

EXAMPLE I

A 50 mL bomb was charged with 3.88 mL of decane (dried over molecular sieves and distilled) and 30 mg of bis(ethylene)pentamethylcyclopentadienyl iridium. The resulting solution contained 0.39 mole percent catalyst. The bomb was flushed with dry ethylene to remove air and then charged with ethylene to an initial pressure of 150 psi. The contents of the sealed bomb (which initially included about 20 mmole each of decane and ethylene) were held at about 200° C. and 260 psi pressure for 60 hours. Analysis of the liquid reaction product by gas chromatography gave the following results (mole percentages):

| | |
|---|---|
| 1-decene | 0.61% |
| 2-decene | 1.82% |
| 3-decene | 2.00% |
| 4- & 5-decenes | 2.13% |
| Total | 6.56% |
| Turnovers = 6.56/0.39 = 16.8 | |

$^1$H NMR analysis of the liquid confirmed this turnover ratio. Gas chromatographic analysis of the ethylene gas removed from the bomb at the conclusion of the run showed 6.2 mole % of ethane.

EXAMPLE II

Bis(ethylene)pentamethylcyclopentadienyl iridium (30 mg) and decane (2.83 g) (pretreated with $H_2SO_4$ to remove olefins, passed through silica gel and distilled under nitrogen) were charged to a 45 mL screw top Parr bomb. The closed bomb was pressured to 150 psi with ethylene, shaken and the pressure released. The bomb was shaken again without ethylene pressure. This procedure was repeated several times to degas the solution. The bomb was then pressured with ethylene to 150 psi at room temperature and placed in a 250° C. bath. The temperature was held between 240° and 250° C. for 19 hours. The pressure at 246° C. was 340 psi. The bomb was allowed to cool. The liquid was clear and brownish-yellow. Some dark material coated the bottom of the bomb. 2.27 Grams of solution was recovered. Gas chromatography of the gas (ambient temperature, POROPAK Q 3 m×⅛ inch) showed 16.65, 16.92 and 18.36 area % ethane, on samples taken sequentially as the solution was outgassing. G. C. showed the product contained 16 weight percent decenes, the isomer distribution of which was as follows:

| | |
|---|---|
| 4- & 5-decene | 31.22% |
| 3-decene | 30.25% |
| 2-decene | 29.17% |
| 1-decene | 9.58% |

The run showed 40 turnovers of the reaction:

$$C_2H_4 + n\text{-}C_{10}H_{22} \rightarrow C_2H_6 + n\text{-}C_{10}H_{20}$$

An additional group of peaks appeared at higher retention time in the gas chromatographic trace of the liquid. Total area % of these peaks was 1%. They have about the same retention time as an authentic sample of 1,3- decadiene and thus the peaks are believed to represent isomeric decadienes.

EXAMPLE III

In this run, reaction was carried out photochemically between pentane and bis(ethylene)pentamethylcyclopentadienyl iridium in a sealed NMR tube. This iridium complex (10 mg) was added to an NMR tube attached to a vacuum stopcock. The air was evacuated from the tube and 0.5 mL of dry pentane was vacuum transferred into the tube. The system was allowed to stand at room temperature under ultraviolet light overnight. The pentane was removed by vacuum, and toluene-d8 NMR solvent was vacuum transferred to the tube. The tube was sealed and the contents subjected to $^1$H NMR. The NMR spectrum showed showed characteristic hydride and allylic resonances indicating attack by the complex on the C-H bonds of pentane, elimination of ethane and a second C-H insertion on coordinated pentene to produce isomeric forms of hydridopentenylpentamethylcyclopentadienyl iridium. Thus although free alkene was not used in this run, it demonstrates the operability of the photochemical process.

EXAMPLE IV

A sample of bis(ethylene)pentamethylcyclopentadienyl iridium was charged to a pipe bomb containing pentane. After 15 hours at 140° C., some free ethylene was noted in the $^1$H NMR spectrum. After 19 hours at 170° C., $^1$H NMR (90 MHz) showed new peaks in the olefin region. Thus operability of the thermolytic reaction between the complex and pentane was demonstrated even though free alkene was not included in the system as a hydrogen acceptor.

EXAMPLE V

A 45 mL Parr screw cap type bomb was charged with dicarbonylpentamethylcyclopentadienyl iridium (30 mg, 78 micromoles) and decane (4.4 g). The solution was degassed by several pressurization/depressurization cycles with ethylene. The bomb was kept at 200° C. and 200 psig for 19 hours. No ethane was found in the gas phase. The temperature was raised to 250° C. and pressure of 240 psig. After 20 hours, the gas was 1.2% ethane. This corresponds to 2.4 turnovers.

EXAMPLE VI

A 45 mL Parr screw cap type bomb was charged with cyclooctadienepentamethylcyclopentadienyl iridium (30 mg, 69 micromoles) and decane (3.45 g). The solution was degassed by repeated pressurization with ethylene to 150 psig and depressurization. The bomb was pressured to 150 psig and heated to 225° C. at which temperature the pressure was 310 psig. After 15 hours, the bomb was cooled and the gas sampled. The gas was 0.28% ethane indicating about one turnover.

EXAMPLE VII

Bis(ethylene)pentamethylcyclopentadienyl iridium (20 mg, 52 micromoles) and cyclooctane (8 mL, 59 mmoles) were charged to a 45 mL screw top Parr bomb. The solution was degassed by several pressurization cycles with ethylene to 150 psig. The bomb was then pressured to 300 psig at 225° C. After 16 hours, the bomb was cooled and the gas sampled. Gas chromatographic analysis of the liquid indicated 0.54% cyclooctene.

It can thus be seen that this invention makes it possible to convert abundant paraffinic or cycloparaffinic hydrocarbons or any mixtures thereof into olefinic or cycloolefinic hydrocarbons or mixtures thereof. Depending on the saturated hydrocarbons used, the process thus may be used as a source of olefins for oxo process conversion to detergent and plasticizer alcohols as well as for making alkylated benzenes for the detergent industry. In addition, olefins suited for use in the manufacture of synthetic lubricants and lubricating oil additives (e.g., detergents and corrosion inhibitors) or for use as comonomers in the production of copolymers of ethylene can be formed by means of the process of this invention.

It will be understood and appreciated that the saturated hydrocarbons (i.e., the open chain paraffins and cyclic paraffins) used as reactants in the process may contain substituents or functionality so long as the conversion of the reactant to an olefin of the same skeletal configuration is not prevented by the substituents or functionality. For example, paraffins and cycloparaffins carrying a trialkylsilyl substituent, such as decyltrimethylsilane, dodecyltrimethylsilane, cyclooctyltrimethylsilane, and the like, are deemed suitable for use in the process. Similarly, ethylbenzene, propylbenzene and other paraffins and cycloparaffins having aromatic substituents may be used to produce such products as styrene, propenylbenzene and the like.

As this invention is susceptible to considerable variation in its practice without departing from its true spirit and scope, it is not intended that this invention be limited by the exemplifications given hereinabove. Rather, what is intended to be covered is encompassed by the appended claims and the equivalents thereof.

What is claimed is:

1. A process of transforming saturated hydrocarbon catalytically into olefinic hydrocarbon which comprises transferring hydrogen from the saturated hydrocarbon to an alkene via a bis(alkene)cyclopentadienyl iridium molecular complex catalyst in the presence of free alkene so that olefinic hydrocarbon corresponding in skeletal configuration to the saturated hydrocarbon is formed.

2. A process of claim 1 wherein the free alkene and the alkene of the molecular complex are ethylene.

3. A process of transforming saturated hydrocarbon catalytically into olefinic hydrocarbon which comprises reacting the saturated hydrocarbon with a bis(alkene)cyclopentadienyl iridium molecular complex in the presence of free alkene so that olefinic hydrocarbon corresponding in skeletal configuration to the saturated hydrocarbon is formed.

4. A process of claim 3 wherein the reaction is performed photochemically under irradiation with ultraviolet light.

5. A process of claim 3 wherein the reaction is performed thermolytically under application of heat.

6. A process of claim 3 wherein the catalyst is charged to the reaction as preformed bis(alkene)cyclopentadienyl iridium molecular complex.

7. A process of claim 3 wherein the catalyst is formed in situ in the reaction mixture via displacement of ligand from a cyclopentadienyl iridium molecular complex containing the displaceable ligand.

8. A process of claim 3 wherein the free alkene and the alkene of the molecular complex are ethylene.

9. A process of transforming saturated hydrocarbon catalytically into olefinic hydrocarbon which comprises reacting the saturated hydrocarbon with a bis(alkene)pentamethylcyclopentadienyl iridium molecular complex in the presence of free alkene so that olefinic hydrocarbon corresponding in skeletal configuration to the saturated hydrocarbon is formed.

10. A process of claim 9 wherein the molecular complex is bis(ethylene)pentamethylcyclopentadienyl iridium.

11. A process of claim 9 wherein the saturated hydrocarbon is predominantly alkane hydrocarbon.

12. A process of claim 9 wherein the saturated hydrocarbon is predominantly cycloalkane hydrocarbon.

* * * * *